(12) United States Patent
Whitbourne et al.

(10) Patent No.: US 8,287,590 B2
(45) Date of Patent: **\*Oct. 16, 2012**

(54) MEDICATED STENT HAVING MULTI-LAYER POLYMER COATING

(75) Inventors: Richard J. Whitbourne, Rochester, NY (US); Alexandra M. Chamberlain, Rochester, NY (US); Daniel G. Hullihen, Caledonia, NY (US); Scott F. Rosebrough, Avon, NY (US); Mildred Calistri-Yeh, Webster, NY (US)

(73) Assignee: Angiotech BioCoatings Corp.

( \* ) Notice: Subject to any disclaimer, the term of this patent is extended or adjusted under 35 U.S.C. 154(b) by 0 days.

This patent is subject to a terminal disclaimer.

(21) Appl. No.: 12/828,512

(22) Filed: Jul. 1, 2010

(65) Prior Publication Data

US 2010/0331967 A1    Dec. 30, 2010

Related U.S. Application Data

(63) Continuation of application No. 10/662,877, filed on Sep. 16, 2003, now Pat. No. 7,771,468, which is a continuation-in-part of application No. PCT/US02/08039, filed on Mar. 18, 2002.

(60) Provisional application No. 60/276,089, filed on Mar. 16, 2001.

(51) Int. Cl.
*A61F 2/06* (2006.01)
(52) U.S. Cl. ...................................... 623/1.44; 623/1.42
(58) Field of Classification Search ......... 623/1.42–1.48
See application file for complete search history.

(56) References Cited

U.S. PATENT DOCUMENTS

| | | | |
|---|---|---|---|
| 4,391,797 A | 7/1983 | Folkman et al. |
| 4,531,933 A | 7/1985 | Norton et al. |
| 4,723,957 A | 2/1988 | Magruder et al. |
| 4,733,665 A | 3/1988 | Palmaz |
| 4,800,882 A | 1/1989 | Gianturco |
| 4,886,062 A | 12/1989 | Wiktor |
| 5,001,009 A | 3/1991 | Whitbourne |
| 5,069,899 A | 12/1991 | Whitbourne et al. |
| 5,294,448 A | 3/1994 | Ring et al. |
| 5,331,027 A | 7/1994 | Whitbourne |
| 5,380,299 A | 1/1995 | Fearnot et al. |
| 5,523,092 A | 6/1996 | Hanson et al. |
| 5,525,348 A | 6/1996 | Whitbourne et al. |
| 5,609,629 A | 3/1997 | Fearnot et al. |
| 5,620,738 A | 4/1997 | Fan et al. |
| 5,707,385 A | 1/1998 | Williams |
| 5,716,981 A | 2/1998 | Hunter et al. |

(Continued)

FOREIGN PATENT DOCUMENTS

EP    0294905    6/1988

(Continued)

OTHER PUBLICATIONS

J. Eduardo Sousa, MD, titled "New Frontiers in Cardiology Drug-Eluting Stents: Part 1", Clinical Cardiology: New Frontiers, Part 1, Circulation, pp. 2274-2279, May 16, 2003.

(Continued)

*Primary Examiner* — Julian Woo
(74) *Attorney, Agent, or Firm* — Angiotech

(57) ABSTRACT

This invention relates to stents having medicated multi-layer hybrid polymer coatings, useful for the treatment of stenosed vasculature or other body passages.

17 Claims, 1 Drawing Sheet

U.S. PATENT DOCUMENTS

| | | | |
|---|---|---|---|
| 5,733,925 | A | 3/1998 | Kunz et al. |
| 5,779,673 | A | 7/1998 | Roth et al. |
| 5,797,898 | A | 8/1998 | Santini, Jr. et al. |
| 5,800,412 | A | 9/1998 | Zhang et al. |
| 5,837,008 | A | 11/1998 | Berg et al. |
| 5,840,329 | A | 11/1998 | Bai |
| 5,843,172 | A | 12/1998 | Yan |
| 5,851,217 | A | 12/1998 | Wolff et al. |
| 5,866,619 | A | 2/1999 | Sintov et al. |
| 5,873,904 | A | 2/1999 | Ragheb et al. |
| 5,882,335 | A | 3/1999 | Leone et al. |
| 5,962,620 | A | 10/1999 | Reich et al. |
| 5,972,027 | A | 10/1999 | Johnson |
| 5,977,163 | A | 11/1999 | Li et al. |
| 5,980,550 | A | 11/1999 | Eder et al. |
| 5,997,517 | A | 12/1999 | Whitbourne |
| 6,071,305 | A | 6/2000 | Brown et al. |
| 6,074,659 | A | 6/2000 | Kunz et al. |
| 6,086,547 | A | 7/2000 | Hanssen et al. |
| 6,096,070 | A | 8/2000 | Ragheb et al. |
| 6,110,483 | A | 8/2000 | Whitbourne et al. |
| 6,171,609 | B1 | 1/2001 | Kunz |
| 6,197,051 | B1 | 3/2001 | Zhong |
| 6,251,136 | B1 | 6/2001 | Guruwaiya et al. |
| 6,254,632 | B1 | 7/2001 | Wu et al. |
| 6,268,390 | B1 | 7/2001 | Kunz |
| 6,273,908 | B1 | 8/2001 | Ndondo-Lay |
| 6,273,913 | B1 | 8/2001 | Wright et al. |
| 6,306,176 | B1 | 10/2001 | Whitbourne |
| 6,306,421 | B1 | 10/2001 | Kunz et al. |
| 6,335,029 | B1 | 1/2002 | Kamath et al. |
| 6,344,035 | B1 | 2/2002 | Chudzik et al. |
| 6,368,611 | B1 | 4/2002 | Whitbourne |
| 6,395,326 | B1 | 5/2002 | Castro et al. |
| 6,403,635 | B1 | 6/2002 | Kinsella et al. |
| 6,491,666 | B1 | 12/2002 | Santini, Jr. et al. |
| 6,491,938 | B2 | 12/2002 | Kunz et al. |
| 6,515,009 | B1 | 2/2003 | Kunz et al. |
| 6,515,016 | B2 | 2/2003 | Hunter |
| 6,599,928 | B2 | 7/2003 | Kunz et al. |
| 6,616,765 | B1 | 9/2003 | Castro et al. |
| 6,656,162 | B2 | 12/2003 | Santini, Jr. et al. |
| 6,663,662 | B2 | 12/2003 | Pacetti et al. |
| 6,699,281 | B2 | 3/2004 | Vallana et al. |
| 6,783,543 | B2 | 8/2004 | Jang |
| 7,041,130 | B2 | 5/2006 | Santini, Jr. et al. |
| 7,052,488 | B2 | 5/2006 | Uhland |
| 7,135,039 | B2 | 11/2006 | De Scheerder et al. |
| 7,771,468 | B2 * | 8/2010 | Whitbourne et al. ......... 623/1.44 |
| 2002/0018795 | A1 | 2/2002 | Whitbourne et al. |
| 2002/0082680 | A1 | 6/2002 | Shanley et al. |
| 2002/0123801 | A1 | 9/2002 | Pacetti et al. |
| 2004/0063805 | A1 | 4/2004 | Pacetti et al. |
| 2004/0166140 | A1 | 8/2004 | Santini, Jr. et al. |
| 2005/0181977 | A1 | 8/2005 | Hunter et al. |
| 2005/0283228 | A1 | 12/2005 | Stanford |
| 2006/0129231 | A1 | 6/2006 | De Scheerder et al. |

FOREIGN PATENT DOCUMENTS

| | | |
|---|---|---|
| EP | 0850604 | 7/1998 |
| EP | 0950386 | 10/1999 |
| EP | 1261297 | 12/2002 |
| JP | 9099056 | 4/1997 |
| JP | 2000-51367 | 2/2000 |
| JP | 2000-1255 | 7/2001 |
| WO | WO-93/16687 | 9/1993 |
| WO | WO-93/17669 | 9/1993 |
| WO | PCT/US94/12128 | 8/1994 |
| WO | WO-94/21308 | 9/1994 |
| WO | WO-95/003036 | 2/1995 |
| WO | WO-98/17331 | 4/1998 |
| WO | WO-98/19713 | 5/1998 |
| WO | WO-98/23228 | 6/1998 |
| WO | WO-98/36784 A1 | 8/1998 |
| WO | WO-00/32255 A1 | 6/2000 |
| WO | WO-01/15526 A1 | 3/2001 |
| WO | WO-01/36008 | 5/2001 |
| WO | WO-01/67991 A1 | 9/2001 |
| WO | WO-02/074194 | 9/2002 |
| WO | WO-03/035135 | 1/2003 |
| WO | WO-03/063924 | 7/2003 |

OTHER PUBLICATIONS

Von Birgelen, C. et al., "The Jostent Coronary Stent Graft—Just another Stent? . . . How Should it be Implemented ?", Abstract: 825-4, ACC 2004/4 9th Annual Scientific Session, Mar. 12-15, 2000, Anaheim, CA, USA.

Concise Encyclopedia of Polymer Science and Engineering, Ed. J. I. Kroschwitz, p. 458-459, 1990.

Rohm & Haas, "ACRYLOID Acrylic Resins for Industrial Finishing", Bulletin 82A4, Sep. 1985.

Rohm & Haas, "PARALOID Thermoplastic Solution Grade & Solid Grade Acrylic Resins for Industrial Finishing", Bulletin 82A37, p. 1-46 (Jun. 1998).

Lincoff et al., Local Delivery of Dexamethasone by Eluting Stent Attenuates the Adverse Response to Biodegradable Polymer in Porcine Coronary Artery. 1993. *Circulation*. vol. 88, No. 4, Part 2, p. 1-655.

Dev et al., Microspheres for Drug Delivery to the Arterial Wall: A Study of Kinetics, Toxicity and Effects of Corticosteroid Loaded Microspheres. 1994. *JACC*. p. 194.

\* cited by examiner

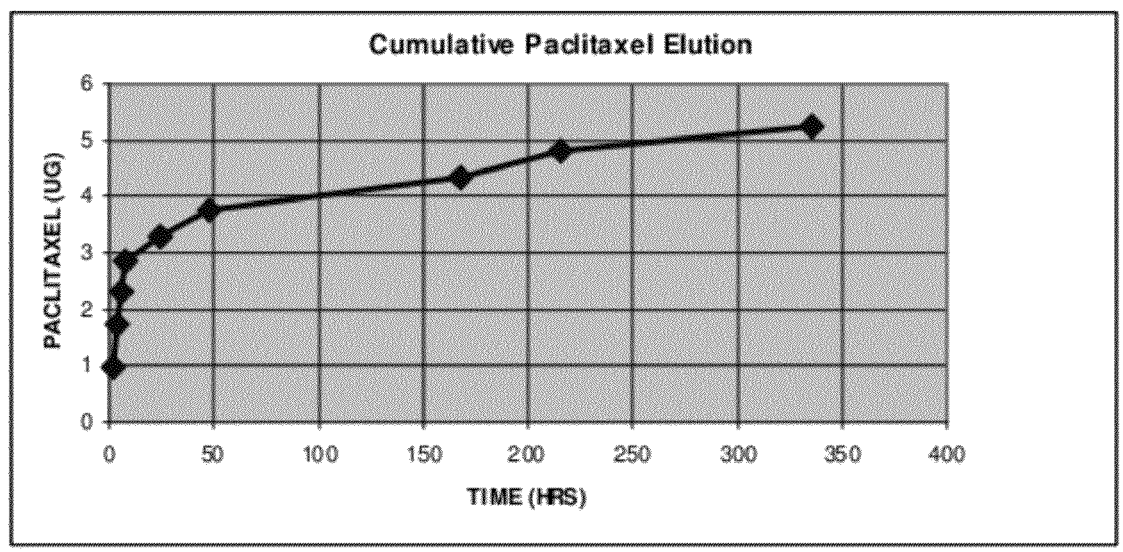

MEDICATED STENT HAVING MULTI-LAYER POLYMER COATING

CROSS-REFERENCE TO RELATED APPLICATIONS

This application is a continuation of U.S. patent application Ser. No. 10/662,877, filed Sep. 16, 2003 now U.S. Pat. No. 7,771,468, which is a continuation-in-part of International Patent Application No. PCT/US02/08039, filed on Mar. 18, 2002, which claims priority to U.S. Provisional Application No. 60/276,089, filed on Mar. 16, 2001, all of which are hereby incorporated by reference.

FIELD OF THE INVENTION

This invention relates to stents having medicated multi-layer hybrid polymer coatings, useful for the treatment of stenosed vasculature or other body passages.

BACKGROUND OF THE INVENTION

Angioplasty procedures have dramatically increased as a treatment for occluded arteries. However, vessels often experience reclosure following the angioplasty procedure. The closure of vessels following angioplasty is known as restenosis. The process of restenosis can occur in over 30% of the cases, depending upon the vessel location, lesion length, as well as other variables.

Restenosis may be caused in some cases by simple mechanical reflex; e.g. caused by the elastic rebound of the arterial wall and/or by dissections in the vessel wall caused by the angioplasty procedure. These mechanical problems have been mitigated somewhat by the use of stents to hold open and prevent elastic rebound of the vessel, and reducing the level of restenosis for many patients. The stent is typically introduced by catheter into a vascular lumen and expanded into contact with the stenosed vascular lesion, thereby providing internal support for the vessel wall. Examples of stents, which have been used in the clinics include stents disclosed in U.S. Pat. No. 4,733,665 issued to Palmaz, U.S. Pat. No. 4,800,882 issued to Gianturco, and U.S. Pat. No. 4,886,062 issued to Wiktor which are incorporated herein by reference in their entirety.

Another aspect of restenosis is believed to be a natural healing reaction to the injury of the arterial wall that is caused by the angioplasty procedure. The final result of the complex steps of the healing process is intimal hyperplasia, the migration and proliferation of medial smooth muscle cells, until the vessel is again occluded.

Stents are typically tubular metallic devices, which are thin-metal screen-like scaffolds, and are inserted in a compressed form and then expanded at the target site. The stents are intended to provide long-term support for the expanded vessel, to keep it from restenosing over time. Unfortunately, initial data from the clinic indicates that the stent implants are not entirely successful in their mission, and in as many as 30% or more of the cases, the vessel restenoses within one year. It would be desirable to have medication(s) available on the stent surface to cope with problems, which arise on the stent surface or in adjacent patient tissue.

When coronary stents are placed, patients often are subjected to aggressive anti-thrombogenic, anti-platelet regimes in order to prevent thrombus formation on the stent surfaces. Thrombus formation on stent surfaces can be a natural consequence of placement of metal objects in the vasculature. It is recognized that the thrombi formed on stents may break loose from the stent, and produce undesired and dangerous occlusions elsewhere in the vasculature. Unfortunately, an aggressive anti-thrombogenic regime compromises a patient's ability to heal injuries that accompany the stenting procedure or other collateral procedures that may have been required. Thus, it is desirable that methods be found that reduce the need for the aggressive anti-thrombogenic therapy associated with coronary stent placement.

To address these problems, various approaches have been proposed. In EP 0 706 376 B1, Burt, et al, proposed that paclitaxel could be incorporated in polymeric layers. Examples included polycaprolactam, poly (lactic-co-glycolic acid), and others. However, many of these layers are biodegradable, and may thus depend upon the enzymatic composition of the patient. It is known that the enzymatic compositions vary considerably from patient to patient. It is thus likely that the biodegradation process and drug release rate would occur at different rates from patient to patient. Furthermore, the polymers used in this disclosure possess inferior adhesion for this application.

U.S. Pat. No. 5,837,008, Berg, et al., U.S. Pat. No. 5,851,217, Wolff, et al., U.S. Pat. No. 5,873,904, Ragheb, et al., and U.S. Pat. No. 6,344,035, Chudzik, et al., describe incorporation of drugs in multiple layers of a single polymer on stents, wherein the drug-polymer layers are applied in one or more consecutive applications. Polymers listed include bioabsorbable and biostable examples. Bioabsorbable examples listed include poly (L-lactic acid), poly(lactide-co-glycolide), and poly(hydroxybutyrate-co-valerate). Drugs listed include heparin and other anticoagulant agents, glucocorticoid or other anti-inflammatory agents, and various anti-replicate agents. Bioabsorbable polymers may depend on the enzymatic composition of the patient, and may be subject to patient to patient variation in drug release. Also, such polymers possess inferior adhesion for this application. Biostable polymers listed include silicone, polyurethanes, polyesters, vinyl homopolymers and copolymers, acrylate homopolymers and copolymers, polyethers, and cellulosics. Furthermore, the use of a single polymer in the drug release layer limits the drug release dynamics to that enabled by the specific polymer used in the layer, and is thus less able to regulate the drug release dynamics to the same extent as is possible using hybrid polymer layers. Further, optimizing drug release dynamics does not provide a coating with the necessary adhesion and flexibility to be clinically acceptable on a stent.

It has been proposed to provide stents, which are seeded with endothelial cells. In one experiment, sheep endothelial cells that had undergone retrovirus-mediated gene transfer for either bacterial beta-galactosidase or human tissue-type plasminogen activator were seeded onto stainless steel stents and grown until the stents were covered. The cells could therefore able to be delivered to the vascular wall where they could provide therapeutic proteins. Other methods of providing therapeutic substances to the vascular wall include simple heparin-coated metallic stents, whereby a heparin coating is ionically or covalently bonded to the stent.

U.S. Pat. No. 5,843,172 to Yan, describes a porous metallic stent in which medication is loaded into the pores of the metal. The stent may also have a polymeric cover, which would contain a different drug than the drug that was loaded into the metal pores. This has the ability to deliver more than one drug, but the ability to mediate the drug release dynamics is limited by the fact that only one type of polymer is used, and the drug in the metallic pores is not bound in a polymeric medium. It has been found that the use of pores without polymer entrapment of the drug results in the drug release rate/profile being entirely dependent on the drug solubility.

Finally, Von Bergelen et al. "The JOSTENT™ Coronary Stent Graft-Just Another Stent? . . . or How Should it be Implanted?", Abstract: 825-4, ACC 2000/49th Annual Scientific Session, Mar. 12-15, 2000, Anaheim, Calif., USA, describes a sleeve of two stents with an ultra thin PTFE tube there between, which was implanted in 24 patients who had suffered acute coronary ruptures. This method mandates the use of oversized high-pressure balloon catheters to achieve adequate expansion of this new coronary stent graft (CSG). In addition, the endoprosthsesis must be accurately sized and placed to avoid occlusion of side branches originating from the target lesion segment, and thrombus formation is a concern.

Thus, there is a need for technology that can consistently provide therapeutic activity from the surfaces of stents in order to reduce the incidence of restenosis and thrombus formation after coronary stenting procedures in the clinic.

SUMMARY OF THE INVENTION

Prior coatings have inferior adhesion and flexibility during stent expansion because they are based on applying the drug(s) without a polymer binder, but instead over-coating it with a separate covering polymer layer which is used to control the drug elution rate. In addition, they use covering single polymer layers that have physical porosity that must be carefully controlled in order to control the drug elution rate(s).

Prior coatings also do not provide drug-containing layers with useful cohesion. Therefore, even though polymer layers cover the drug layers, the drug layers can break up in the direction orthogonal to the device surface, causing catastrophic adhesion failures. Up to 40% of the drug can be lost during stent expansion with prior drug layer coatings. (G. W. Stone, May 5, 2003 TCTMD e-letter)

The inventive coatings use a primer system with at least two polymers, preferably a hydrophilic and a hydrophobic polymer, that allows outstanding adhesion to metal substrates and the flexibility to meet the demanding requirements of vascular stents. The inventive hybrid coatings use a drug delivery layer which permits the loading and elution control of virtually any drug or combinations of drugs from the surface of a stent. This provides a valuable drug delivery platform which can be modified slightly to adapt to different substrate materials and shapes, and to different active agents, without major modifications. The inventive hybrid polymer binder controls the drug elution rate by using various ratios of hydrophilic polymer to hydrophobic polymer, the combination stabilizing the drug during manufacturing, sterilization, and deployment of the stent. The hybrid polymer matrix or alloy allows control of the elution rate with less need to control layer thickness as compared to previous efforts. Moreover, there is no drug loss upon expansion with stents coated according to the instant invention.

Numerous different drugs have been incorporated into the coatings, including popular anti-restenosis drugs such as paclitaxel, to demonstrate an ability to control the loading and elution of these drugs from the surface of the stent. Another important property for adequate stent coating is the mechanical requirements of the coating. To meet the extremely challenging mechanical requirements necessary for successful stent coating requires exceptional flexibility and adhesion to achieve. The inventive coatings provide these properties.

In one embodiment, the present invention comprises a stent on which multiple polymer layers are applied to the stent surfaces, at least one (but not all) of which polymer layers provide reservoirs for a variety of individual drugs or drug cocktails. The polymer layers may be hybrid polymer layers, and may serve different purposes in the multi-layer stent coating.

The polymer layers of the invention typically comprise a bonding or primer layer, which can be applied directly onto the metallic stent surface. An intermediate polymer layer optionally can be applied over the primer layer. The intermediate polymer layer is used to enhance the flexibility, elasticity, and expandability of the composite hybrid polymer layers. Next, one or more drug carrier polymer layers can be applied over the intermediate layer, or if an intermediate layer is not used, directly onto the primer layer. One or more of the polymer layers may be a hybrid polymer layer. As used herein, a hybrid polymer layer is one in which two or more different polymers are combined forming a layer, which is a homogeneous polymeric alloy. In the instant invention, a primer hybrid polymer contains polymers designed to provide anchorage to the stent surface. An intermediate hybrid polymer layer contains polymers capable of imparting enhanced flexibility and elasticity to the coating composite and adhesion to the primer and to the drug release layers. The drug release layer preferably is also a hybrid polymer layer, but contains different polymers from those used in the other two layers.

The polymer layers of the invention possess excellent flexibility and elasticity, and they are expandable, so as to remain intact following sterilization, implantation in the patient, and stent expansion. The polymer layers are not significantly bioerodable, so that differences in hormonal activity from patient to patient are minimized. The polymer layers can regulate drug release dynamics because hydrophilic and hydrophobic polymers are employed.

The drug-loaded layers of the invention provide technology for entrapping therapeutic drug mixtures in designed, biocompatible, hybrid polymer layers. In one embodiment of the invention, the polymer layers serve as reservoirs for the drugs, and protect and stabilize the drugs during sterilization and storage. The polymer layers can be porous to body fluids, such that the drugs can become solubilized via diffusion of body fluids into the polymer layers, with subsequent diffusion of the solubilized drugs out of the layers at controlled rates. The polymer-drug layers can be deposited over the polymeric coated stent scaffolds, which can be deliverable to stenosed lesions via catheters, such as in the manner currently practiced in the clinic. The polymer layers are designed to provide efficacious drug concentrations for appropriate time periods at the stenosed site. For example, drug-polymer layers may provide fast drug release for about one to three days, followed by a slower sustained drug release rate for one week, two weeks, 30 days or longer, as needed. The sum of the periods of fast and slow release may be referred to as a sustained period. The drug release layers can also be designed to provide different drug release rate profiles, if desired, by for instance adjusting the ratio of hydrophilic to hydrophobic polymers in the polymer drug release layer.

In one embodiment of the invention, the polymer layers comprise polymeric alloys of polyvinylpyrrolidone, cellulose esters, and polyurethanes, acrylate polymers and copolymers, polyethylene glycols, polyethylene oxides, hydrophilic acrylate polymers and copolymers, melamines or epoxides in order to alter diffusion dynamics, or to enhance physical properties such as adhesion, flexibility, and abrasion resistance by varying the components in the casting solution (especially the ratio of hydrophilic to hydrophobic polymers). It is contemplated that for a faster drug release, a higher ratio of hydrophilic polymer to hydrophobic polymer would be used and visa versa to slow the drug release.

In another embodiment of the invention, the surface properties of the coating can be further influenced by its relative composition, having varying degrees for example, from highly lubricious to essentially non-lubricious. By including pharmacological agents in the surface layer, the surface can become a drug reservoir and provide high regional drug concentrations, while systemic concentrations remain low. Such polymeric alloys are described herein, and also in U.S. Pat. No. 5,069,899, Whitbourne, et al., titled "Anti-thrombogenic, anti-microbial compositions containing heparin;" U.S. Pat. No. 5,525,348, Whitbourne, et al., titled "Coating compositions comprising pharmaceutical agents;" U.S. Pat. No. 6,086,547, Hanssen, et al., titled "Wire for medical use coated with polyether sulphone and a copolymer;" and U.S. Pat. No. 6,110,483, Whitbourne, et al., titled "Adherent, flexible hydrogel and medicated coatings;" published PCT international application WO 01/15526 titled "Anti-infective covering for percutaneous and vascular access devices and coating method;" U.S. Ser. No. 09/442,891, filed Nov. 18, 1999, titled "Flexible sealed coil-like devices;" and U.S. Ser. No. 60/196,781, provisional application filed Apr. 13, 2001, titled "Targeted therapeutic agent release devices and methods of making and using the same," which are incorporated herein by reference.

The coating composition can be used to coat a variety of stents. Non-limiting examples include: either self-expanding stents (such as the Wallstent variety), or balloon-expandable stents (as are available in a variety of styles, for instance, Gianturco-Roubin, Palmaz-Shatz, Wiktor, Strecker, Cordis, AVE Micro Stent, Boston Scientific Nir stent, and Guidant MULTI-LINK® coronary stent). The stents are typically prepared from materials such as stainless steel or tantalum, or nitinol. They have various mesh patterns having sharp edges, and are shorter or longer and have lower or higher diameters. The coatings of the invention are suitable for all such stents and others known to those of skill in the art or to be subsequently developed.

One embodiment of the invention relates to a medicated stent having a coating comprising: (a) a primer layer comprising a first composition of one or more polymers, optionally a combination of hydrophilic and hydrophobic polymers, and (b) a drug reservoir layer comprising a polymeric matrix of a second composition of one or more polymers, optionally a combination of at least one hydrophilic polymer and at least one hydrophobic polymer, the polymer composition of the drug reservoir layer being distinct from the polymer composition of the primer layer, and the drug reservoir layer further comprising one or more active agents, the coating remaining intact upon stent expansion and during a sustained period thereafter, and releasing efficacious amounts of the active agent at the site of insertion and stent expansion in a subject.

In another embodiment, the medicated stent can further comprise an intermediate layer between the primer layer and the drug release layer, comprising a polymer composition distinct from the polymer composition of the primer and drug reservoir layers. This medicated stent may further comprise one or more image enhancing material(s) in one of the layers, or in a separate layer(s), that is capable of enhancing visibility if the device under ultra sound, magnetic resonance imaging, X ray imaging, and/or other imaging modality.

The medicated stent may comprise different agents that are contained within the same and/or different layers. The primer layer and/or the drug reservoir layer may be a single layer or may comprise two or more layers. Moreover, the intermediate layer may comprise multiple layers. The medicated stent may comprise more than one active agent.

In yet another embodiment, the primer layer comprises one or more polymers selected from the group consisting of acrylate polymer/copolymer, acrylate carboxyl and/or hydroxyl copolymer, polyvinylpyrrolidone/vinylacetate copolymer (PVP/VA), olefin acrylic acid copolymer, ethylene acrylic acid copolymer, epoxy polymer, polyethylene glycol, polyethylene oxide, polyvinylpyridine copolymers, polyamide polymers/copolymers polyimide polymers/copolymers, ethylene vinylacetate copolymer and/or polyether sulfones. The intermediate layer may comprise one or more polymers selected from the group consisting of acrylate polymer/copolymer, acrylate carboxyl and/or hydroxyl, PVP/VA, polyurethane, silicone urethane polymer, polycarbonate urethane polymer, polyvinylbutyral, and/or epoxy polymers.

The primer and/or intermediate and/or drug reservoir layer may comprise one or more polymer selected from the group consisting of polyurethane, polycarbonate urethane polymer, and silicone urethane polymer.

In a further embodiment, the medicated stent may comprise one or more polymers having a flexural modulus greater that 1000 psi and elongation at break greater than 200%. The medicated stent may have a drug reservoir layer comprising a polymer selected from acrylate polymer/copolymer, acrylate hydroxyl and/or carboxyl copolymer, polyvinyl pyrrolidone (PVP), PVP/VA, cellulose ester, polyurethane, polycarbonate-urethane polymer, silicone-urethane polymer, epoxy polymer, polyethylene glycol and/or polyethylene oxide. The medicated stent may have a drug reservoir comprising one or more polyurethanes, cellulose nitrate, and/or one or more other cellulose ester polymer(s).

In a further embodiment, the medicated stent may have a drug reservoir layer comprising one or more polymers selected from acrylate polymer/copolymer, acrylate polymer/copolymer containing carboxyl and/or hydroxyl groups, cellulose nitrate and/or other cellulose ester. The medicated stent may have an active agent comprising an anti-restenotic agent effective at a stented site. The total coating thickness may be between about 0.3 and about 30 microns. The medicated stent may also have a primer layer having a thickness between about 0.01 and 5 or 0.1 and about 5 microns, and the drug reservoir layer having a thickness of between about 0.1 and about 10 microns. Moreover, the medicated stent may comprise an intermediate layer having a thickness between about 0.1 and about 15 microns.

In other embodiments of the invention, the active agent is selected from one or more of anti-thrombogenic agents, anti-inflammatory agents, antineoplastic agents, anti-proliferative agents, cytostatic agents, cytotoxic agents, antimicrobial agents, anti-restenotic agents, anti-platelet agents, and anti-coagulant agents. The active agent may also be selected to from one or more of anti-fibrin and fibrinolytic agents, anti-platelet agents, prostacyclins (and analogues), glycoprotein IIb/IIIa agents, thromboxane inhibitors, anti-thrombin and anti-coagulant agents, anti-mitotic, antiproliferative and cytostatic agents, antiangiogenic and angiostatic agents, ACE inhibitors, growth factor antagonists, antioxidants, vitamins, calcium channel blockers, fish oil (omega 3-fatty acid), phosphodiesterase inhibitors, nitric acid donor, Somatostatin analogues, immunosuppressive agents and antiinflamatory agents, antimicrobials, radionuclides including alpha, beta and gamma emitting isotopes, COX-2 inhibitors, endothelial promoters, kinase inhibitors, epidermal growth factor kinase inhibitors, tyrosine kinase inhibitors, MAP kinase inhibitors, protein transferase inhibitors, alone or in combinations.

In a further embodiment, the active agent may be selected from one or more of plasmin, streptokinase, single chain urokinase, urokinase, t-PA (tissue type plasminogen activator), aminocaproic acid, aspirin, monoclonal antibodies, peptides, drugs (e.g. ReoPro, Cilastagel, eptifibatide, tirofiban, ticlopidine, Vapiprost, dipyridamole, forskolin, angiopeptin, argatroban, dextan, heparin, LMW heparin, heparin complexes, Enoxaparin, Dalteparin, hirudin, recombinant hirudin, anti-thrombin, synthetic antithrombins, thrombin inhibitors, Warfarin, other coumarins, vincristine, vinblastine, paclitaxel and its analogues, methotrexate, cisplatin, fluorouracil, rapamycin, sirolimus, tacrolimus, everolimus, azathioprine, cyclophosphamide, mycophenolic acid, corticosteroids, colchicine, nitroprusside, paclitaxel, angiostatin and endostatin; genetic materials, oligonucleotides, Cilazapril, Lisinopril, Captopril, VEGF, FGF, Probucol, Tocopherol, nifedipine, dipyridamole, Molsidomine, angiopeptin, prednisolone, glucocorticoid, dexamethasone, rifamycin, Re-188, Re-186, 1-125, Y-90 celecoxib, Vioxx, dipyridamole, theophylline, alone or in combinations.

In another embodiment, the medicated stent may have a primer layer comprising one or more of acrylate/carboxyl polymer, epoxy polymer, polyvinylpyrrolidone vinylacetate copolymer (PVP/VA). The primer layer may also comprise one or more of ethylene acrylic acid copolymer (EAA), epoxy polymer, and polycarbonate urethane.

In yet a different embodiment of the invention, the intermediate layer may comprise polycarbonate polyurethane. The medicated stent may have a drug release layer comprising one or more of acrylate/carboxyl polymer, epoxy polymer, and polyvinylpyrrolidone vinylacetate copolymer (PVP/VA). The drug release layer may comprise nitrocellulose. The drug release layer may also comprise nitrocellulose and one or more of polytetramethylene ether glycol urethane, polycarbonate-urethane, silicone-urethane polymer, polyethylene glycol, polymethylmethacrylate-2-hydroxyethylmethacrylate copolymer, polyethylmethacrylate-2-hydroxyethylmethacrylate copolymer, polypropylmethacrylate-2-hydroxyethylmethacrylate copolymer, polybutylmethacrylate-2-hydroxyethylmethacrylate copolymer, polymethylacrylate-2-hydroxyethylmethacrylate copolymer, polyethylacrylate-2-hydroxyethylmethacrylate copolymer, polypropylacrylate-2-hydroxymethacrylate copolymer, polybutylacrylate-2-hydroxyethylmethacrylate copolymer, methylvinylether maleicanhydride copolymer, and poly(2-hydroxyethyl methacrylate). The active agent may be selected from the group consisting of paclitaxel, heparin complexes, rifamycin, and methotrexate.

Another aspect of the invention relates to a method for making a medicated stent having struts becoming separated upon stent expansion, comprising: applying a primer polymer liquid comprising one or more polymers in a volatile medium, applying a drug reservoir polymer liquid comprising one or more polymers in a volatile medium, the one or more drug reservoir polymers being different from the one or more primer layer polymers, and applying an active agent either together with or after applying the drug reservoir polymer liquid, and removing the volatile media, the layers being applied without forming coating bridges between struts of the stent, the layers remaining intact upon stent expansion, and releasing efficacious amounts of the active agent at the site of stent expansion. Other embodiments may require more than one active agent to be applied or repeating one or more of the applying steps. The invention may involve application of an intermediate flexibilizing polymer liquid comprising one or more polymers that differ from the one or more polymers of the primer layer and the drug reservoir layer. The volatile media may have a boiling point greater than about 110 degrees C. The liquids may have a viscosity between about 20 and about 70 cps.

In yet another aspect, the invention relates to a method for making a medicated stent comprising applying a primer polymer layer and a drug reservoir layer comprising at least two polymers and one or more active agent(s), wherein the polymer compositions of the primer and drug reservoir are different, without forming coating bridges between struts of the stent, the coating remaining intact upon stent expansion, and releasing efficacious amounts of the active agent(s) at the site of stent expansion.

In a further aspect, the invention relates to a method for administering a bioactive agent to a target site in a subject, comprising: implanting a stent at the target site of the subject, the stent comprising a coating having a primer layer and a drug release layer, the drug release layer comprising the bioactive agent, and the primer and drug release layers comprising different polymers, expanding the stent, and allowing the bioactive agent to elute from the coating during an extended period, the coating remaining intact during implanting, during stent expansion, and during the extended period.

The drug release layer may comprise an ionic heparin complex, and at least one other bioactive agent that is not anti-thrombogenic such as an anti-angiogenic factor, an immunosuppressing agent, an antimicrobial agent, an anti-inflammatory agent, an anti-restenotic agent and combinations. The active agent may comprise heparin together with at least one anti-restenotic drug selected from the group consisting of paclitaxel, rapamycin sirolimus, tacrolimus, and everolimus. The active agent may be selected from the group consisting of heparin complexes and/or one or more of paclitaxel, rifamycin, and methotrexate, and/or combinations. The active agents may be benalkoniumheparinate and paclitaxel.

The primer layer can comprise an ethylene acrylic acid copolymer and an epoxy polymer, wherein the ethylene acrylic acid copolymer can be one or more of PRIMACOR® 5989 and 5990. The epoxy can be one or more of EPOTUF® 38-505, EPOTUF® 37-618, and EPON 1001.

The drug reservoir layer may include a polyurethane and a cellulose nitrate. The polyurethane may be polytetramethylene ether glycol urethane and/or polycarbonate urethane. Examples of polyurethane include Chronoflex AR, Chronoflex AL, Chronoflex C, and Bionate 80A.

The primer layer may comprise an ethylene acrylic acid copolymer and an epoxy polymer and the drug reservoir layer comprises a polyurethane and a cellulose ester.

The invention also relates to a medicated stent having a coating comprising a primer layer comprising a first composition of one or more polymers, and a drug reservoir layer comprising an alloy of a second composition of more than one polymer, the first composition being distinct from the second composition, with one or more active agents, the polymers of the second composition protecting and stabilizing the one or more active agents during sterilization and storage, the coating having sufficient adhesion and flexibility to remain intact upon stent expansion and during a sustained period thereafter, and releasing efficacious amounts of the active agent at the site of stent expansion.

The invention also relates to a medicated stent comprising: a stent body, a biologically active agent, means for containing and controllably releasing the agent from the stent over an extended period, comprising a first polymer, and means for bonding the containing means to the stent body, comprising a second polymer, the containing and bonding means remaining intact upon stent expansion and during the extended period.

The elements of the invention recited herein may be combined or eliminated among the particular embodiments described, as would be apparent to a person of ordinary skill.

BRIEF DESCRIPTION OF THE DRAWINGS

FIG. 1, which contains data from Table 1, Example 1 shows the cumulative quantity of paclitaxel eluted, in micrograms, over a period of 336 hours (14 days). Approximately 10% of the paclitaxel eluted out over a period of 14 days. The total amount of eluted drug and length of elution time are influenced by the amount of or the number of coatings of the drug releasing layer, the hydrophilicity of the layer(s), and the solubility of the drug(s) in the medium into which it/they are being released.

DETAILED DESCRIPTION OF THE INVENTION

In describing preferred embodiments of the present invention, specific terminology is employed for the sake of clarity. However, the invention is not intended to be limited to the specific terminology so selected. It is to be understood that each specific element includes all technical equivalents, which operate in a similar manner to accomplish a similar purpose. The embodiments of the invention may be modified or varied, and elements added or omitted, without departing from the invention, as appreciated by those skilled in the art in light of the above teachings. Each reference cited here is incorporated by reference as if each were individually incorporated by reference.

In order to develop a hybrid polymer delivery system for targeted therapy, it is important to be able to control and manipulate the properties of the system both in terms of its physical and drug release characteristics. The active agents can be imbibed into a surface hybrid polymer layer, or incorporated directly into the hybrid polymer coating solutions. Imbibing drugs into surface polymer layers is an efficient method for evaluating polymer-drug performance in the laboratory, but for commercial production it may be preferred for the polymer and drug to be premixed in the casting mixture. Greater efficacy can be achieved by combining the two elements in the coating mixtures in order to control the ratio of active agent to polymer in the coatings. Such ratios are important parameters to the final properties of the medicated layers, i.e., they allow for better control of active agent concentration and duration of pharmacological activity.

Typical polymers used in the drug-release system can include water-insoluble cellulose esters, various polyurethane polymers including hydrophilic and hydrophobic versions, hydrophilic polymers such as polyethylene glycol (PEG), polyethylene oxide (PEO), polyvinylpyrrolidone (PVP), PVP copolymers such as vinyl acetate, hydroxyethyl methacrylate (HEMA) and copolymers such as methylmethacrylate (PMMA-HEMA), and other hydrophilic and hydrophobic acrylate polymers and copolymers containing functional groups such as carboxyl and/or hydroxyl.

Cellulose esters such as cellulose acetate, cellulose acetate propionate, cellulose acetate butyrate, cellulose acetate phthalate, and cellulose nitrate may be used. The cellulose ester preferably serves as a polymer component in the hybrid polymer compositions. Cellulose nitrate is preferred because of its compatibility with the active agents and its ability to impart non-tackiness and cohesiveness to the coatings. Cellulose nitrate has been shown to stabilize entrapped drugs in ambient and processing conditions. Cellulose nitrate (nitrogen content=11.8-12.2%) preferably is used in this invention, although grades of the polymer having lower nitrate concentrations could be used. Viscosity grades, such as 3.5, 0.5 or 0.25 seconds, are used in order to provide proper rheological properties when combined with the coating solids used in these formulations. Higher or lower viscosity grades could be used. However, the higher viscosity grades can be more difficult to use because of the high viscosities that obtain at the solids concentrations preferred in this invention. Lower viscosity grades, such as 3.5, 0.5 or 0.25 seconds, preferably are used in order to provide proper rheological properties when combined with the coating solids used in these formulations. Physical properties such as tensile strength, elongation, flexibility, and softening point are related to viscosity (molecular weight) and can decrease with the lower molecular weight species, especially below the 0.25 second grades.

The cellulose derivatives comprise anhydroglucose structures. Cellulose nitrate is a hydrophobic, water-insoluble polymer, and has high water resistance properties. This structure leads to high compatibility with many active agents, accounting for the high degree of stabilization provided to drugs entrapped in cellulose nitrate. The structure of nitrocellulose is given below:

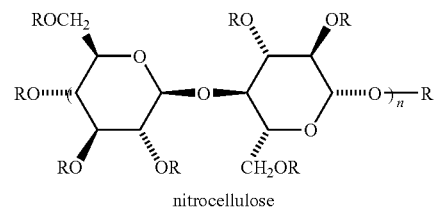

nitrocellulose $R = NO_2$ or H

Cellulose nitrate is a hard, relatively inflexible polymer, and has limited adhesion to many polymers that are typically used to make medical devices. Also, control of drug elution dynamics is limited if only one polymer is used in the binding matrix, since the stent has significant variables such as coating thickness and the ratio of polymer to entrapped drug. In one embodiment, this invention uses polyurethane polymers with cellulose nitrate in the hybrid polymer drug loaded matrix. Polyurethanes provide the hybrid polymer matrix with greater flexibility and adhesion to the polymer coated stent surfaces of the invention. Polyurethanes can also be used to slow the drug elution from coatings. Aliphatic, aromatic, polytetramethylene ether glycol, and polycarbonate are among the polyurethanes, which can be used in the coatings.

From the structure below, it is possible to see how more or less hydrophilic polyurethane polymers may be created based on the number of hydrophilic groups contained in the polymer structures. The polyurethanes used in the invention are water-insoluble, flexible, and compatible with the cellulose esters.

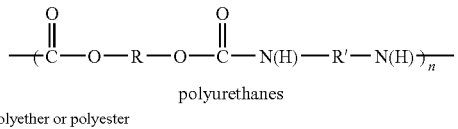

polyurethanes

R = polyether or polyester
R' = aliphatic or aromatic

Polyvinylpyrrolidone (PVP) is a polyamide that possesses unusual complexing and colloidal properties and is essentially physiologically inert. PVP and other hydrophilic polymers are typically biocompatible. PVP is incorporated in drug loaded hybrid polymer compositions in order to increase drug release rates. In one embodiment, the concentration of PVP that is used in drug loaded hybrid polymer compositions can be less than 20%. This concentration would not make the layers bioerodable or lubricious. In addition, PVP concentrations from <1% to greater than 80% are deemed workable.

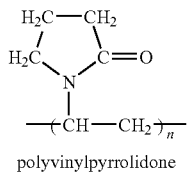

polyvinylpyrrolidone

Acrylate polymers and copolymers including polymethylmethacrylate (PMMA) and polymethylmethacrylate hydroxyethyl methacrylate (PMMA/HEMA) are known for their biocompatibility as a result of their widespread use in contact and intraocular lens applications. Some work describing the use of such copolymers in drug release coatings for stents has been reported in the literature. The coating was found to provoke very little smooth muscle and endothelial cell growth, and very low inflammatory response (Bar). These polymers/copolymers are compatible with drugs and the other polymers and layers of the instant invention.

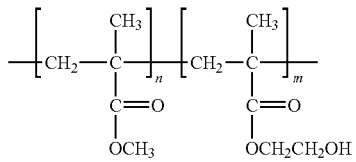

Methylmethacrylate hydroxyethylmethacrylate copolymer

The drug-loaded coatings can be prepared as coating solutions in organic solvents. The solutions are non-reactive and can have a shelf life of up to 18 months when stored at room temperature. Among others, simple procedures (such as dipping or spraying, followed by air-drying) can be used to apply the hybrid polymer surfaces to stents. Drying the devices at elevated temperatures (40 to 120° C.) can remove the residual solvents to produce biocompatible surface layers of approximately 0.3 to 30 microns thick. Once dried, the surface layers are stable for substantially the life of the sterile packaging, generally three to five years, depending on the drug(s) entrapped in the hybrid polymer layer, and on the storage conditions.

The polymers used in the primer layer may be cross-linkable and the coating may comprise a cross-linker for the polymers, such as epoxy resin, melamine resin, other amino resin, and phenolic resins. The polymers may be selected from a carboxyl function acrylic polymer, hydroxyl function acrylic polymer, amine function acrylic polymer, methylol function, and amide function acrylic polymer. They may be a cross-linkable acrylic selected from methylmethacrylate, butylmethacrylate, isobutylmethacrylate, ethylmethacrylate, methylacrylate, ethylacrylate, butyl acrylate acrylic acid, methacrylic acid, styrene methacrylate, and styrene acrylate, and copolymers thereof, and other non-acrylic polymers such as polyurethanes, polycarbonate-urethanes, silicone-urethanes, aliphatic polyurethanes, polyvinyl pyridine copolymers, polyethylene glycol, polyethylene oxide, polyamide copolymer, polyimide copolymer, other polymers known to those of skill in the art may be used in the primer layer.

The primer layer comprises hydrophobic polymers that are preferably water-insoluble polymers that do not significantly react with the hydrophilic polymers in solution, have low water absorption, provide a high degree of flexibility, and have improved bonding to stent substrates. Suitable commercial products that may be used in the invention include acrylics such as ACRYLOID® (Rohm & Haas) AT-63, AT-51, AT-81, WR-97; ethylene acrylic acid copolymers such as PRIMACOR™ (DOW) 5989, 5990; melamine resins such as CYMELO® hexamethoxymethylmelamine (CYTEC Industries) 303, 370, 380; epoxies such as EPON (Shell) 1001; and polyvinylbutyral such as BUTVAR B-79 (Monsanto), polyurethanes such Tecoflex 93A, Chronoflex AR. The preferred acrylic stabilizing polymers include reactive groups such as hydroxyl or carboxyl that can react with epoxies but do not render the polymer hydrophilic.

In one embodiment, the inventive coating includes a hydrophilic polymer used in the primer and/or the drug reservoir layer(s), such as a water soluble polyolefin such as a hydrophilic vinyl polymer having polar pendant groups, a polyacrylate or methacrylate having hydrophilic esterifying groups, a polyether, a polyethylene glycol, or other polymer with hydrophilic characteristics as known in the art. The hydrophilic polymer is preferably PVP or PVP/vinyl acetate such as PVP/VA (GAF) E-335 and E-635.

The hydrophilic component may be of any of the classes discussed in Concise Encyclopedia of Polymer Science and Engineering, Kroschwitz, ed. (Wiley 1990), pp. 458-59, which is incorporated herein by reference. Polymers such as polyvinylpyrrolidone, polyethylene glycol, polyethylene oxide, or polyvinyl alcohol are acceptable, alone or in combination. Examples of suitable hydrophilic polymers include homopolymers or copolymers of the following compounds: polyolefins such as vinyl polymers having polar pendant groups, N-vinylpyrrolidone, N-vinyllactam, N-vinyl butyrolactam, N-vinyl caprolactam, sodium styrene sulfonate monomer, 2-acrylamido-2-methylpropane sulfonic acid, sodium vinyl sulfonate, vinyl pyridine, acrylates or methacrylates having hydrophilic esterifying groups. Other hydrophilic polymers include polyethers, polyethylene glycol, polysaccharides, hydrophilic polyurethanes, polyhydroxyacrylates, polymethacrylates, and copolymers of vinyl compounds and hydroxyacrylates or acrylic acid, so long as the appropriate hydrophilicity is present. Other examples include dextran, xanthan, hydroxypropyl cellulose, methyl cellulose, polyacrylamide, and polypeptides. Other hydrophilic components are known to persons of skill in the art.

The invention may require acrylics, e.g. polymers and copolymers of acrylic acid and methacrylic acid and esters thereof, as defined for example in ACRYLOID Thermoplastic Acrylic Ester Resins for Industrial Finishing, Rohm & Haas, Bulletin 82A37 (1987), including cross-linkable acrylics with at least one component containing carboxyl, hydroxyl, amide, or methylol groups. The following ACRYLOID polymers with functional groups given are preferred: AT-51 (hydroxyl), AT-63 (hydroxyl), AT-81 (carboxyl), and WR-97 (hydroxyl). Cross-linkable acrylic emulsions such as RHOPLEX B-15J (Rohm & Haas), and styrene acrylic emulsions such as AROLON® 820-W-49 (Reichhold) may also be used.

A variety of polymers may be used, e.g., epoxy resins, particularly cured epoxy polymers such as EPOTUF® 38-505 (Reichhold), and preferably those cured with polyamide, such as EPOTUF® 37-618 (Reichhold), vinyl polymers, particularly vinyl acetate, vinyl acetals such as polyvinyl butyral, and ethylene vinyl acetate copolymers. Other appropriate polymers having the requisite characteristics will be apparent to persons of ordinary skill. The polymers preferably, but not necessarily, contain reactive groups or points of reactivity such as hydroxyls, mono-, di- and tertiary amines, acids such as carboxyl, amides, or other groups which represent points of chemical reactivity. In the case of the acrylics, this is referred to as having a "functionality" that is cross-linkable. The polymers and points of chemical reactivity are able to form attractive forces such as hydrogen bonding toward the medical device surface, and also toward the hydrophilic polymer and/or bioactive agent. Such bonds are very strong, and provide desirable adhesion and flexibility to the coating presumably without requiring covalent, ionic, or other links.

Polymers with reactive groups are preferred in the primer layer with stents, which present a metal substrate. However, polymers lacking such groups such as acrylic or styrene copolymers may also be used effectively. The reactive groups can also react to form a cross-linked matrix or help to form a cross-linked matrix. If desired, cross-linkers such as urea resins, melamines, isocyanates, phenolics, and others may be incorporated to interact with the points of chemical reactivity on the polymer chains to cross-link the polymers of the invention with themselves. Alternatively, cross-linkers may react with themselves as stabilizing polymers to form a cross-linked matrix in which the hydrophilic polymer is enmeshed, resulting in an adherent, flexible coating. Cross-linking is useful in promoting effective adhesion by ensuring that the solvents do not attack and degrade the polymer layer excessively when subsequent layers are applied.

The drug reservoir layer, which can be referred to as the polymeric drug-release or the drug loaded layer, comprises mixtures of more and less hydrophilic polymers. Hydrophobic polymers comprise cellulose esters such as cellulose nitrate, polycarbonate-urethanes, acrylate polymers and copolymers with or without functional groups such as those previously cited in this disclosure and others known to those of skill in the art. Hydrophilic polymers comprise vinyl polymers with hydrophilic pendant groups such PVP and its copolymers, polyethylene glycol, polyethylene oxide, HEMA, HEMA-acrylate and methacrylate copolymers, and other hydrophilic polymers/copolymers previously cited in this disclosure and others known to those of skill in the art.

In the primer layers, the term anchoring polymers is used to describe those that provide anchoring to metal substrates, typically those with functional groups, such as amides, carboxyl, hydroxyl, amine, imine, amide, imide, sulfoxyl, and sulfonyl.

Cross-linking and cross-linkable polymers may be added to the anchoring polymer in the primer layer. Examples include epoxy resins, melamine resins, phenolics, isocyanate polymers. Other polymers may be included as needed to impart desirable properties of adhesion, cohesion, durability, and flexibility. These include polyethylene ethylene glycols, polyethylene oxide, and polyvinylpyridine polymers and copolymers.

In the drug releasing layer, the term stabilizing polymers is intended to describe those which protect active agents during high temperatures encountered in curing and sterilizing coated stents. These include cellulose esters and ethers, acrylic polymers and copolymers and others that can be determined by a person of ordinary skill to prevent degradation of active agents during preparation and sterilization of coatings.

The term toughening polymers is used to describe those which impart desirable physical properties of toughness, durability, and flexibility in expansion and use. Examples include polyurethanes.

The drug reservoir layer may also include other relatively hydrophilic polymers that impart other desirable physical properties, such as to control elution, and improve flexibility, and to reduce hydrophobicity. These include relatively hydrophilic polymers such as hydroxyethyl methacrylate, acrylic HEMA (polyhydroxyethyl methacrylate/methylmethacrylate) copolymers, polyvinyl pyrrolidone, PVP-VA copolymers, polyethylene glycols, and polyethylene oxides. Thus, the drug stabilizing matrix generally comprises polymers of relatively hydrophilic and hydrophobic character.

The active agents may be integrated in the polymer matrix, meaning that they are alloyed with, and deposited throughout the polymer matrix. This is a preferable arrangement in contrast to active agents that are imbibed into a drug reservoir layer, or are deposited before applying a polymer layer on top of a drug.

The coatings of the present invention are extremely durable, even when subjected to adhesion and flexing tests, as shown in the examples. Such enhanced adhesion and flexibility is a surprising result. The coatings according to the invention may be applied to the surface of a biomedical device or other device with sufficient thickness and permanence to retain the coating's desirable qualities throughout the useful life of the coated device. The coatings of the invention are nonreactive with living tissue and are non-thrombogenic in blood. They are not substantially biodegradable.

The coatings of the invention may be thin, on the order of 0.9 to 100 microns, preferably less than about 50 or 30 microns, and coherent in that they form a continuous surface layer on the stent as manufactured, and retain the coherence on the stent after expansion. They are resistant to removal on prolonged soaking in aqueous fluids, and are adherent to a wide variety of substrates.

The coatings may be applied by various techniques such as dip, pour, pump, spray, brush, wipe, or other methods known to those skilled in the art. The coating solutions have low viscosities, typically less than 100 CPS, and have good spreading properties. The coatings are preferably baked at elevated temperatures, typically 50 degrees C. to 140 degrees C., to drive off the organic solvents. It may be necessary to treat some surfaces like polyethylene with gas plasma or other ionizing treatment to promote interaction with the coating and adhesion to the substrates.

The coating may contain polymers in addition to the stabilizing polymer such as polyurethane, polyester, styrene polybutadiene, polyvinylidene chloride, polycarbonate, and polyvinyl chloride, preferably in the inner layer to promote adhesion to the surface of the device.

Anti-Restenosis and Other Active Agents

Examples of active agents that can be combined with the hybrid polymer carrier layers of the invention include antifibrin and fibrinolytic agents, including plasmin, streptokinase, single chain urokinase, urokinase, t-PA (tissue type plasminogen activator), aminocaproic acid; anti-platelet agents including, aspirin, prostacyclins (and analogues); glycoprotein IIb/IIIa agents including monoclonal antibodies, peptides (e.g. ReoPro, Cilastagel, eptifibatide, tirofiban, ticlopidine, Vapiprost, dipyridamole, forskolin, angiopeptin, argatroban), thromboxane inhibitors; anti-thrombin and anti-coagulant agents, including dextan, heparin, LMW heparin (Enoxaparin, Dalteparin), hirudin, recombinant hirudin, anti-thrombin, synthetic antithrombins, thrombin inhibitors, Warfarin (and other coumarins); anti-mitotic, antiproliferative and cytostatic agents, including vincristine, vinblastine, paclitaxel, methotrexate, cisplatin, fluorouracil, rapamycin, azathioprine, cyclophosphamide, mycophenolic acid, corticosteroids, colchicine, nitroprusside; antiangiogenic and angiostatic agents, including paclitaxel, angiostatin and endostatin; genetic materials and oligonucleotides; ACE inhibitors (e.g. Cilazapril, Lisinopril, Captopril); growth factor (e.g. VEGF, FGF) antagonists; antioxidants and vitamins (e.g. Probucol, Tocopherol); calcium channel blockers (e.g.

nifedipine); fish oil (omega 3-fatty acid); phosphodiesterase inhibitors (e.g. dipyridamole); nitric acid donor (e.g. Molsidomine); somatostatin analogues (e.g. angiopeptin); immunosuppresives and anti-inflammatory agents (e.g. prednisolone, glucocorticoid and dexamethasone); antimicrobials (e.g. rifamycin) and radionuclides, including alpha, beta and gamma emitting isotopes (e.g. Re-188, Re-186, I-125, Y-90); COX-2 inhibitors such as Celecoxib and Vioxx; kinase inhibitors, such as epidermal growth factor kinase inhibitor, tyrosine kinase inhibitors, MAP kinase inhibitors protein transferase inhibitors, Resten-NG, and other biologically active agents and biologic response modifiers, and others, alone or in combinations to exert multiple actions simultaneously in order to prevent restenosis, and provide other desired biological effects.

The coating may comprise combinations of active agents, e.g., coatings which contain both an anti-thrombogenic agent to protect against thrombus and an anti-restenotic agent. Generally for example, heparin complexes are combined with other bioactive agents, for example in a cellulose ester-containing layer, along with other bioactive agents that are not anti-thrombogenic, such as heparin together with anti-restenotic agents. Advantageously, in such an embodiment, the elution rates of the agents are not affected by the presence of the other agent(s). Thus, the anti-thrombogenic effect can be achieved in conjunction with the anti-restenotic effect without interference between the agents. This is an unexpected advantage because generally these types of bioactive agents would be expected to interfere with each other's elution rate in a polymer coating. Because the inventive coatings permit co-elution without interference, they provide a solution to the long unresolved problem of thrombus formation on stents, which results in some patient deaths following stent placement.

The amount of active agent loaded in coatings which have been produced according to the invention has been in the range of about 25 to about 600 micrograms, although lower and higher loadings may be used depending on a variety of factors, including the drug, the desired dosage level, the drug release layer composition, the type of stent, the diameter and length of stent, the number of layers and how the active agent is applied, the coating thickness, the chemical characteristics of the active agent, and other factors. These factors are adjusted to provide a durable coating that controllably releases the desired amount of active agent over an extended period. In a typical desired release pattern, 25% of the active agent is released in the first few days, the remainder being released gradually over 30 or more days. Other release patterns may readily be achieved using the inventive methods and compositions, depending on the therapeutic effect desired (e.g., anti-angiogenesis, anti-cancer, etc.).

The hybrid polymer layers of the invention possess physical properties that enable their useful application on stents. For instance, the hybrid polymers of the invention achieve excellent adhesion on the metallic stent surfaces. The adhesion of the hybrid polymer layers of the invention is made possible by the use of certain bonding layers as described in U.S. Pat. No. 5,997,517, incorporated herein by reference in its entirety.

Furthermore, the hybrid polymers of the invention, together with the multi-layer composite structure, ensure that the drug layers will remain well adhered to the stent surface, even during expansion of the stent, and will not lose their adhesion during prolonged implantation. The polymers of the invention do not alter the mechanical stent functions, such as forces required for expansion and strength so that the stent will resist collapsing after implantation.

In one embodiment of the invention, the production of stents can begin with the application of the bonding primer layer. In one embodiment, the primer layers can be on the order of about 0.1 to about 5 microns thick. Cross-linked primer layers can be thinner than non-cross-linked layers. The primer layer can be applied by dipping the stent in the primer coating solution, followed by drying at elevated temperatures in order to drive off the solvents in the coating solution, and to cure and cross-link the primer layer.

The primer layer may be subjected to turbulent airflow to open any bridging that occurs prior to the curing step. It is also possible to spray the primer coating onto the stent. Typical curing schedules include drying for fifteen to sixty minutes at 100° C. to 120° C. The hybrid polymer primer layers comprise polymeric alloys that include such polymers and copolymers as acrylate polymers and copolymers, especially those having functional groups including amine, hydroxyl, and carboxyl, etc., epoxy resins, amine resins, ethylene acrylic acid copolymers, polyurethanes (especially more hydrophobic versions), copolymers of polyvinylpyrrolidone such as with vinyl acetate, polyether sulfones, and others.

The use of one or more intermediate layers is optional, although preferred. The intermediate layer can be applied over the primer layer using substantially the same methods as described for the primer layer, including similar curing schedules at elevated temperatures. The intermediate layer is employed to enhance the flexibility, elasticity, and expandability properties of the composite coating layers. It is recognized that thin layers in a composite when constructed appropriately will acquire the properties of its components. The intermediate layer is intended to contribute to and enhance the flexibility, elasticity, and expandability properties of the composite layers. An example of a polymer which performs well in this role is a polycarbonate-polyurethane having a flexural modulus (1% secant modulus (psi) (ASTM procedure D790)) greater than 1,000 or 3,000, and elongation at break greater than 200% or 300%. In a typical embodiment, the primer layer preferably would be about 0.1 to about 5 microns thick, and the intermediate layer would be about 0.1 to about 15 microns thick. This is because it is intended that the ultra flexible intermediate layer contributes substantially to the flexibility of the composite coating, and therefore preferably is at least as thick as the adjacent layers.

In practice, the invention employs polymers and copolymers which are useful in the intermediate layer and include vinyl acetals, especially polyvinyl butyral, polyurethanes which are more flexible and elastic and expandable, polycarbonate polyurethanes are especially useful for this purpose, acrylate polymers and copolymers which are elastic, flexible, and expandable. Other polymers and copolymers could also be used in this application, provided that they contribute the appropriate physical properties, are compatible and adherent to the adjacent layers, and are biocompatible.

The drug releasing hybrid polymer layer can comprise two or more polymers, together with one or more drugs, which can be dissolved in an organic solvent or solvent mixture. The drug(s) are usually dissolved in the organic solvent mixture, but may also be present as dispersions of solid particles. The hybrid polymer matrix forms a polymeric alloy upon drying. In the preferred embodiment, this layer can be typically about 1 to about 10 microns thick. The hybrid polymer matrix can be applied as one layer, or as two or more layers, and different drugs may be present in the same or different layer(s). When multiple layers are employed, the different layers could have the same or different drug release properties.

Soluble drugs can also form into the polymeric alloy at the molecular level. An organic solvent or solvent mixture can be selected so that it is a mutual solvent for the polymeric and soluble drug components, while in the liquid form, and throughout the drying process. It is also preferable if the solvent has the ability to swell the substrate, thereby enabling some of the drug-hybrid polymer components to penetrate superficially into the substrate surface and gain improved adhesion. The polymeric components of the drug releasing layer can comprise cellulose esters to stabilize and preserve the drug components, and usually contain a relatively hydrophilic polyurethane. The polyurethane contributes flexibility, elasticity, and expandability to the drug-releasing layer. Other polymers may also be incorporated into the layer, including hydrophilic, water soluble polymers such polyvinylpyrrolidone (PVP), PVP copolymers, polyethylene glycol, polyethylene oxide water soluble cellulose ethers and esters such hydroxymethylcellulose, others. Drugs selected from the groups that were previously cited may be incorporated, alone or in combinations.

In one embodiment of the invention, the coating solutions are prepared by first dissolving the polymer components in the solvent mixtures. It is also possible to dissolve the individual polymer components separately in solutions, and then to combine together separate solutions of the individual polymers. The drug(s) are then usually incorporated into the hybrid polymer solution, although the drugs can be added before the polymers. The drug releasing coating is then applied over the stent, which already has one, or more polymer coatings, using the same methods as used for the other polymer coatings. After coating, the coating is dried for five to sixty minutes at temperatures of 40° C.-120° C.

The coated stents can be packaged and sterilized. Ethylene oxide is useful for sterilization of stents prepared according to the invention.

The following examples are intended to illustrate embodiments of the invention and are not intended to limit the scope of the invention. It should be understood that the concentrations of the components of the solutions of the examples may be varied within the scope of the invention and that the components may be used in different combinations, and with additional or different polymers as described above.

In coatings of the invention, the primer (bonding) layer uses a polymer combination of
(1) acrylate/carboxyl polymer+epoxy polymer+polyvinylpyrrolidone vinylacetate copolymer (PVP/VA) or
(2) ethylene acrylic acid copolymer (EAA)+epoxy polymer+polycarbonate urethane.

Other polymers may be used in this role, including polyimide copolymers, polyamide copolymers, polyether sulfone polymers, polyethylene glycol polymers, polyethylene oxide polymers, other polymers which typically are used in metal primer applications.

An intermediate layer may be polycarbonate polyurethane, flexible acrylate polymers/copolymers including butyl acrylate, polyvinyl butyral, other elastic polymers used alone or in hybrid polymer combinations.

A drug release layer polymer combinations suitable for use with the invention are acrylate/carboxyl polymer+epoxy polymer+polyvinylpyrrolidone vinylacetate copolymer (PVP/VA), RS Nitrocellulose plus any of the following: polytetramethylene ether glycol urethane, polycarbonate-urethanes, PVP, polyethylene glycol, polyethylene oxide, Methylvinylether maleicanhydride copolymer, and/or Poly(2-hydroxyethyl methacrylate).

Active ingredients used with these combination coatings include paclitaxel, benzalkonium heparinate, rifamycin, and methotrexate These polymer combination and the ratios specified in the examples are not limiting, and other suitable combinations and ratios may be used as long as they provide the desired adhesion and drug release effects of the invention.

In the following examples: Polyurethane 1 is a polycarbonate urethane; Polyurethanes 2 and 3 are polytetramethylene ether glycol urethanes; Cellulose Ester 1 is RS Nitrocellulose, ¼ sec grade; Cellulose Ester 2 is RS Nitrocellulose, 5-6 sec grade. The terms nitrocellulose and cellulose nitrate are also used for these latter compounds.

EXAMPLE 1

The following solutions were prepared:

| Composition 1 | |
|---|---|
| Acrylate/carboxyl polymer, 55.5% solution (1) | 8.33 gm |
| Tetrahydrofuran (THF) | 39.58 gm |
| Cyclohexanone | 41.60 gm |
| PVP/VA Polymer Solution (2) | 2.73 gm |
| Ethanol | 1.37 gm |
| Epoxy Polymer Solution (3) | 1.20 gm |
| Composition 2 | |
| Epoxy Polymer Solution (3) | 2.56 gm |
| PVP/VA Polymer Solution (2) | 2.79 gm |
| Acrylate/carboxyl polymer, 55.5% Solution (1) | 8.50 gm |
| Cyclohexanone | 42.70 gm |
| THF | 36.70 gm |
| Ethanol | 5.56 gm |
| Paclitaxel | 1.00 gm |

(1) This copolymer solution is 55.5% (w/w) solids in aromatic 150/butyl cellosolve, 87.5/12.5.
(2) This copolymer solution is 50.0% (w/w) solids in ethanol.
(3) This epoxy polymer is 75% (w/w) solids in xylene Composition 1 was coated on stainless steel coronary stents, and dried for 60 minutes at 120° C. This layer was applied twice. Composition 2 was then coated over the primer layers, and dried for 60 minutes at 120° C. Drug loading on the stents in the range of 50-60 µg was achieved by applying composition 2 three times and drying after each application. The stent samples with three layers of composition 2 were subjected to elution in room temperature phosphate buffered saline for times up to 336 hours, and produced the following results tabulated in TABLE 1.

TABLE 1

| | Release Characteristics for Paclitaxel Extracts | | | |
|---|---|---|---|---|
| Sample Identification and Elution Time | Analysis #1 Paclitaxel Conc. (µg/ml) | Analysis #2 Paclitaxel Conc. (µg/ml) | Average Paclitaxel in Eluent (µg/ml) | Extract volume (ml) |
| Sample 1, 2 hr. | 0.6 | 0.7 | 0.65 | 1.5 |
| Sample 1, 4 hr. | 0.5 | 0.5 | 0.50 | 1.5 |
| Sample 1, 6 hr. | 0.4 | 0.4 | 0.40 | 1.5 |
| Sample 1, 8 hr. | 0.3 | 0.4 | 0.35 | 1.5 |
| Sample 1, 24 hr. | 0.3 | 0.3 | 0.30 | 1.5 |
| Sample 1, 48 hr. | 0.3 | 0.3 | 0.30 | 1.5 |
| Sample 1, 168 hr. | 0.4 | 0.4 | 0.40 | 1.5 |
| Sample 1, 216 hr. | 0.3 | 0.3 | 0.30 | 1.5 |

TABLE 1-continued

Release Characteristics for Paclitaxel Extracts

| Sample 1, 336 hr. | 0.3 | 0.3 | 0.30 | 1.5 |
|---|---|---|---|---|

| Sample Identification and Elution Time | μg Paclitaxel Released | % of Total Paclitaxel released over 336 hours | Elution Time Cumulative Hrs. | Paclitaxel Release Cumulative μg |
|---|---|---|---|---|
| Sample 1, 2 hr. | 0.98 | 18.6 | 2 | 0.98 |
| Sample 1, 4 hr. | 0.75 | 14.3 | 4 | 1.73 |
| Sample 1, 6 hr. | 0.60 | 11.4 | 6 | 2.33 |
| Sample 1, 8 hr. | 0.53 | 10.0 | 8 | 2.85 |
| Sample 1, 8 hr. | 0.53 | 10.0 | 8 | 2.85 |
| Sample 1, 24 hr. | 0.45 | 8.6 | 24 | 3.30 |
| Sample 1, 48 hr. | 0.45 | 8.6 | 48 | 3.75 |
| Sample 1, 168 hr. | 0.60 | 11.4 | 168 | 4.35 |
| Sample 1, 216 hr. | 0.45 | 8.6 | 216 | 4.80 |
| Sample 1, 336 hr. | 0.45 | 8.6 | 336 | 5.25 |

The data show that approximately 10% of the paclitaxel eluted out over a period of 14 days. The data plotted in FIG. 1 show the cumulative quantity of paclitaxel eluted, in micrograms, over a period of 336 hours (14 days). While not wishing to be bound thereby, it is believed that the rate of drug elution is independent of the number of coated layers, and that the total amount of eluted drug and length of elution time are influenced by the amount of or the number of coatings of the drug releasing layer, the hydrophilicity of the layer(s), and the solubility of the drug(s) in the medium into which it/they are being released.

EXAMPLE 2

This example provides a composite coating of three flexible polymer or hybrid polymer layers. The hybrid polymer bonding layer solution was applied and dried at 120° C. for 60 minutes. An intermediate layer was applied and dried at 120° C. for 60 minutes. The drug release hybrid polymer layer was applied and dried at 75° C. for 60 minutes. A high boiling point solvent was included in each formulation to aid in processing. Drug(s) can be imbibed into the drug release hybrid polymer layer, but the preferred method is to add the active agents to the coating liquid so that the drug/polymer layer can be controlled.
(All values are wt/wt %, unless otherwise specified)

| Bonding layer | |
|---|---|
| Polyurethane 1 | 0.78% |
| EAA | 3.05% |
| Epoxy | 0.90% |
| Dimethyl acetamide (DMAC) | 2.67% |
| Cyclohexanone | 33.66% |
| THF | 58.94% |
| Intermediate layer | |
| Polyurethane 1 | 8.80% |
| DMAC | 66.20% |
| Cyclohexanone | 25.00% |
| Drug release hybrid polymer layer | |
| Polyurethane 2 | 6.07% |
| Cellulose ester 1 | 2.43% |
| THF | 54.64% |
| Ethanol | 21.85% |
| DMSO | 15.01% |

Stent samples coated with this example had good uniformity based on dye testing. Coated stents that were expanded proved quite flexible and demonstrated excellent adhesion to the substrate.

EXAMPLE 3

This example considers a composite coating of three flexible polymer or hybrid polymer layers. A hybrid polymer bonding layer solution was applied and dried at 120° C. for 60 minutes. An intermediate layer was applied and dried at 120° C. for 60 minutes. A drug release hybrid polymer layer, as outlined below, was applied and dried at 75° C. for 60 minutes. The drug release hybrid polymer layer contains one additional, ultra hydrophilic component that was not included in Example 2. It was expected that Example 3 would elute more rapidly relative to Example 2. A high boiling solvent was included in each formulation to aid in processing. This drug release hybrid polymer layer is more susceptible to having the drug imbibed into it from solution than the drug release layer in Example 2. The preferred method is to add the active agents to the coating liquid to achieve better control of the drug/polymer ratio.

| Bonding layer - | |
|---|---|
| Same as Example 2 | |
| Intermediate layer - | |
| Same as Example 2 | |
| Drug release hybrid polymer layer | |
| Polyurethane 2 | 5.05 |
| Polyurethane 3 | 2.17 |
| Cellulose ester 2 | 1.28 |
| THF | 46.75 |
| Ethanol | 29.75 |
| DMSO | 15.00 |

Stent samples coated with this example had good uniformity based on dye testing. Coated stents that were expanded demonstrated good flexibility and adhesion to the substrate, and did not crack.

EXAMPLE 4

This example considers a composite coating of 3 flexible polymer or hybrid polymer layers. A bonding layer solution was applied and dried at 120° C. for 60 minutes. An intermediate layer was applied and dried at 120° C. for 60 minutes. A drug release hybrid polymer layer was applied and dried at 75° C. for 60 minutes. (Example 3 is desirable as compared to Example 5 due to high boiling solvents (e.g., a boiling point over about 110° C.) for processing, and lower viscosity solutions (e.g., about 20-70 cps), which are desired ranges for coating liquids.

| Bonding layer | |
|---|---|
| Polyurethane 1 | 0.80 |
| EAA | 3.90 |
| Epoxy | 1.15 |
| DMAC | 3.40 |
| Cyclohexanone | 15.60 |
| THF | 75.15 |
| Intermediate layer | |
| Polyurethane 1 | 11.7 |
| DMAC | 88.3 |
| Drug release hybrid polymer layer | |
| Polyurethane 2 | 7.14 |
| Cellulose ester 1 | 2.86 |
| THF | 64.29 |
| Ethanol | 25.71 |

The embodiment of Example 3 is preferred over that of Example 4 since high boiling solvents were incorporated in the drug release hybrid polymer layer in that example, which improves processing, makes it easier to prevent the coating from bridging between the struts of the stent, and provides lower solution viscosity.

EXAMPLE 5

This example concerns a composite coating of two flexible polymer or hybrid polymer layers. No bonding layer was applied. Solution was applied and dried at 120° C. for 60 minutes. Drug release hybrid polymer layer was applied and dried at 75° C. for 60 minutes.

| Intermediate layer | |
|---|---|
| Polyurethane 1 | 11.7 |
| DMAC | 88.3 |
| Drug release hybrid polymer layer | |
| Polyurethane 2 | 7.14 |
| Cellulose ester 1 | 2.86 |
| THF | 64.29 |
| Ethanol | 25.71 |

Example 3 is preferred over this example 5 due to improved composite integrity credited to the adhesion imparted by the bonding layer. Specifically, the composite of Example 3 showed strong adhesion to the substrate when abraded by rubbing with a finger when immersed in water at room temperature. The composite coating of this example showed some breakdown/delamination when wet rubbed during water immersion.

EXAMPLE 6

In this example, two drugs (paclitaxel and benzalkonium heparinate) were combined together in the drug release layer and were coated on a stainless steel stent. The bonding layer was applied by dip coating, and excess coating was blown off with nitrogen, and dried for 30 minutes at 100° C. The intermediate layer was applied by dip coating, and excess coating was blown off with nitrogen, and dried for 30 minutes at 100° C. The drug release layer was applied by dip coating, excess coating was blown off with nitrogen, and was dried for 60 minutes at 75° C.

| Bonding layer | | |
|---|---|---|
| Polyurethane 1 | [1] | 0.79% |
| EAA | [2] | 3.06% |
| Epoxy | [3] | 0.90% |
| Cyclohexanone | [4] | 33.64% |
| DMAC | [5] | 2.67% |
| THF | [6] | 58.94% |
| Intermediate layer | | |
| Polyurethane 1 | [7] | 8.80% |
| DMAC | [8] | 66.20% |
| Cyclohexanone | [9] | 25.00% |
| Drug release layer | | |
| Polyurethane 2 | [10] | 5.89% |
| Nitrocellulose 2 | [11] | 2.36% |
| THF | [12] | 53.00% |
| Ethanol | [13] | 21.19% |
| DMSO | [14] | 14.56% |
| Paclitaxel | [15] | 1.00% |
| Benzalkonium heparinate | [16] | 2.00% |

This example showed good coating uniformity, good wet abrasion resistance, and good adhesion to the metal stent surface.

EXAMPLE 7

This example is similar to Example 6, except that the drug release layer contained only benzalkonium heparinate. The coatings were applied on a stainless steel stent using the same procedures as in Example 6.

| Bonding layer - | |
|---|---|
| same as previous examples | |
| Intermediate layer - | |
| same as previous examples | |
| Drug releasing layer | |
| Polyurethane 2 | 5.89% |
| Nitrocellulose 2 | 2.36% |
| THF | 53.00% |
| Ethanol | 21.19% |
| DMSO | 14.56% |
| Benzalkonium heparinate | 3.0% |

This example also showed good coating uniformity, good wet abrasion resistance, and good adhesion to the metal stent surface.

EXAMPLE 8

This example is similar to Example 6, except that the drug release layer contained rifamycin. The coatings were applied on a stainless steel stent using the same procedures as in Example 6.

| Bonding layer - | |
|---|---|
| same as previous examples | |
| Intermediate layer - | |
| same as previous examples | |
| Drue release layer | |
| Polyurethane 2 | 5.89% |
| Nitrocellulose 2 | 2.36% |
| THF | 53.00% |
| Ethanol | 21.19% |

-continued

| | |
|---|---|
| DMSO | 14.56% |
| Rifamycin | 3.00% |

EXAMPLE 9

In this example methotrexate was imbibed into the drug releasing layer from an aqueous solution. The bonding layer and intermediate layer are the same as were used in Example 6, and were applied using the same procedures.

| Bonding layer - | |
|---|---|
| same as above | |
| Intermediate layer - | |
| same as above | |
| Drug release layer | |
| Polyurethane 2 | 6.07% |
| Nitrocellulose 2 | 2.43% |
| THF | 54.64% |
| Ethanol | 21.85% |
| DMSO | 15.01% |

The drug release layer was applied and treated as in Example 8. After the oven curing process, the stent was cooled to room temperature, and then briefly immersed in an aqueous solution of methotrexate, 25 mg/ml., and air dried. The coating absorbed drug from the aqueous solution.

EXAMPLE 10

Stents were coated with the following primer (BOND-COAT®, STS Biopolymers, Inc.) layer and intermediate layer, and dried 15 minutes at 100° C., after each application.

| BOND-COAT ® Primer Layer | |
|---|---|
| Polycarbonate polyurethane | 0.78% |
| Ethylene acrylic acid copolymer | 3.05% |
| Epoxy resin | 0.90% |
| DMAC | 2.67% |
| Cyclohexanone | 33.66% |
| THF | 58.94% |
| Intermediate layer | |
| Polycarbonate polyurethane | 1.28% |
| DMAC | 71.67% |
| Cyclohexanone | 27.05% |

Next, the stent was coated with the following drug reservoir layer, and dried for 15 minutes at 75° C.

| Drug Reservoir Layer | |
|---|---|
| Polycarbonate polyurethane | 2.5 gm |
| Cellulose nitrate | 1.0 gm |
| Methyl ethyl ketone | 30.0 gm |
| n-Butanol | 20.0 gm |
| Dimethylacetamide | 41.4 gm |
| Cyclohexanone | 27.6 gm |
| Paclitaxel | 2.0 gm |
| Silicone polyurethane | 2.5 gm |

This solution coated uniformly, and resulted in a smooth, clear layer.

EXAMPLE 11

A coronary stent was coated with the primer and intermediate layers as in Example 10. Next, the stent was coated with the following drug reservoir layer, and dried using the same schedule as in Example 10.

| Drug Reservoir Layer | |
|---|---|
| Cyclohexanone | 6.29 gm |
| Dimethylacetamide | 4.31 gm |
| n-Butanol | 4.40 gm |
| Polyethylene glycol 3350 | 0.37 gm |
| Cellulose nitrate | 0.15 gm |
| Paclitaxel | 0.015 gm |

This solution coated uniformly, and resulted in a smooth, clear layer.

EXAMPLE 12

A coronary stent was coated with the primer and intermediate layers as in Example 10. Next, the stem was coated with the following drug reservoir layer, and dried using the same schedule as in Example 10.

| Drug Reservoir Layer | |
|---|---|
| Tetrahydrofuran | 7.0 gm |
| Dimethylacetamide | 4.0 gm |
| Cyclohexanone | 6.0 gm |
| Methylvinylether maleic anhydride copolymer | 0.37 gm |
| Cellulose nitrate | 0.03 gm |
| Paclitaxel | 0.015 gm |

This solution exhibited solvent attack on the intermediate layer during coating.

EXAMPLE 13

A coronary stent was coated with the primer and intermediate layers as in
Example 10. Next, the stent was coated with the following drug reservoir layer, and dried using the same schedule as in Example 10.

| Drug Reservoir Layer | |
|---|---|
| Dimethylacetamide | 8.0 gm |
| Benzyl alcohol | 8.0 gm |
| Poly(2-hydroxyethyl methacrylate) | 0.25 gm |
| Paclitaxel | 0.019 gm |

This solution coated uniformly, and resulted in a smooth, clear layer.

EXAMPLE 14

A coronary stent was coated with the primer and intermediate layers as in Example 10. Next, the stent was coated with the following drug reservoir layer, and dried using the same schedule as in Example 10.

| Drug Reservoir Layer | |
| --- | --- |
| Polycarbonate polyurethane | 2.5 gm |
| Cellulose nitrate | 1.0 gm |
| Methyl ethyl ketone | 30.0 gm |
| n-Butanol | 20.0 gm |
| Dimethylacetamide | 18.9 gm |
| Cyclohexanone | 27.6 gm |
| Paclitaxel | 2.0 gm |

This solution coated uniformly, and resulted in a smooth, clear layer.

Stents were expanded and inspected for cracking and adhesion failure. No cracking or chipping off was observed after stent expansion. Several coated stents were incubated in 37° C. phosphate buffered saline (PBS) for various times up to 10 days. Stents were removed from the serum at their designated time points, and soaked in acetonitrile to remove the coating. The acetonitrile extract was tested via HPLC to determine how much paclitaxel remained on each stent after its incubation period. 60.4% of the starting Paclitaxel remained on stents after 10 days of incubation on PBS.

EXAMPLE 15

This comparative example evaluates adhesion of gelatin and human albumin on metal stents.
Experiment
Stainless steel stents were coated with two biodegradable polymer solutions, 5% gelatin and 5% human albumin and tested for adhesion.
Materials
Commercial 15 mm stainless steel stents
VEE GEE 150 Bloom Type A Economix Gelatin, Vyse Gelatin Company
5% human albumin solution, Alpha Therapeutic Corporation
1,1,1 trichloroethane, EM Science
stainless steel tabs, 1 cm×8 cm
Triton X-100 nonionic surfactant, Ruger Chemical Company
Protocol
Prepare a 5% w/w solution of the gelatin by dissolving 5 g of gelatin in 95 g of filtered deionized water. Add 0.4% w/w Triton X-100 by mixing 0.1 g of Triton X-100 to 24.9 g of 5% w/w gelatin solution.

Human albumin comes as a 5% w/v solution. Add 0.4% w/w Triton X-100 by mixing 0.1 g of Triton X-100 to 24.9 g of 5% w/v human albumin solution.

Clean the steel tabs with 1,1,1 trichloroethane then coat with each of the polymer solutions by dip coat methods. Use a 5-second dwell time and approximately 3 cm/s draw speed. Allow samples to air-dry for ½ hour at room temperature then oven dry for one hour at 45° C. Test adhesion using the so-called tape test method, in which a strip of Scotch 810 Tape is firmly pressed onto the coated surface, and then pulled off abruptly. The coated article and the tape are inspected to see if any of the coating was stripped off of the coated surface. No coating should be removed by this test. This test method has been widely accepted for many years by members of the coating industry as a useful predictor of coated product performance in use.

Repeat steel tab procedure using the 15 mm stainless steel stents, except add one step. After drawing the sample from the coating solution use helium to blow any excess polymer off the stent. (Remove any polymer that may be filling the holes in the stent.)

Results/Summary

The coating solutions both produce a uniform coating on the steel tabs. However, the tape dry adhesion tests show that both coatings failed. No other tests were preformed since they failed in the first test.

The coated stents were dyed with a Gentian Violet solution and compared to a dyed uncoated stent. The stent pieces were dipped into the solution and blotted dry with a paper towel. Both the coated stents showed a bright purple color while the uncoated stent did not show the bright purple color. This shows that the stents were covered with the polymer coatings. The samples underwent the dry adhesion tape test and were observed under a microscope. Polymer strands were seen to be coming off, showing the samples failed the adhesion test. No other tests were performed since they failed the first test.

CONCLUSION

The gelatin and human albumin polymers produce coatings that fail to adhere to steel tabs or stainless steel stents. The inventive coatings were far superior.

What is claimed is:

1. A stent having a coating comprising: (a) a primer layer having a polymer composition of two or more polymers, and (b) a single outermost drug reservoir layer having a polymer composition comprising a polymeric alloy mixture of two or more polymers, the primer layer polymer composition being distinct from the drug reservoir layer polymer composition, the drug reservoir layer further comprising one or more active agents, the coating having sufficient adhesion and flexibility to remain intact upon stent expansion and during a sustained period thereafter, and releasing efficacious amounts of the active agent at the site of stent expansion;
wherein the primer layer comprises one or more polymers selected from the group consisting of acrylate polymer/copolymer, acrylate carboxyl or hydroxyl copolymer, olefin acrylic acid copolymer, ethylene acrylic acid copolymer, a polyamide polymer/copolymer, a polyimide polymer/copolymer, polyvinylpyrrolidone/vinyl acetate copolymer (PVP/VA), polyethylene glycol, polyethylene oxide, ethylene vinylacetate copolymer, epoxy polymer, polyurethane, polycarbonate urethane, silicone urethane, a polyvinylpyridine polymer, a polyvinylpyridine copolymer, and polyether sulfones.

2. The stent of claim 1, further comprising an intermediate layer between the primer layer and the drug reservoir layer, the intermediate layer comprising a polymer composition distinct from the primer layer polymer composition and the drug reservoir layer polymer composition.

3. The stent of claim 2, wherein the intermediate layer comprises one or more polymers selected from the group consisting of acrylate polymer/copolymer, acrylate carboxyl and/or hydroxyl copolymer, polycarbonate polyurethane, polyvinylpyrrolidone/vinyl acetate copolymer (PVP/VA), polyurethane, silicone urethane polymer, polycarbonate urethane polymer, polyvinylbutyral, and epoxy polymers.

4. The stent of claim 1, further comprising one or more image enhancing materials in one of the layers, or in one or more separate layers, the image enhancing material being capable of enhancing visibility in ultra sound, magnetic resonance imaging, or X ray imaging.

5. The stent of claim 1, wherein the primer layer polymer composition comprises an anchoring polymer.

6. The stent of claim 1, wherein the drug reservoir polymer composition comprises a drug stabilizing polymer and a toughening polymer.

7. The stent of claim 6, wherein the drug stabilizing polymer is a cellulose ester, a cellulose ether, an acrylic polymer, an acrylic copolymer or combinations thereof.

8. The stent of claim 6, wherein the toughening polymer is a polyurethane.

9. The stent of claim 1, wherein the drug reservoir layer comprises one or more polymers selected from the group consisting of hydroxyethyl methacrylate (HEMA), copolymers of HEMA with acrylate, copolymers of HEMA with polymethylmethacrylate (PMMA), polyvinyl pyrrolidone, polyvinylpyrrolidone/vinyl acetate copolymer (PVP/VA), a polyethylene glycol, acrylate polymer/copolymer, acrylate/carboxyl polymer, acrylate hydroxyl and/or carboxyl copolymer, a cellulose ester, a polyurethane, polycarbonate-urethane polymer, a silicone-urethane polymer, an epoxy polymer, cellulose nitrate, polytetramethylene ether glycol urethane, polymethylmethacrylate-2-hydroxyethylmethacrylate copolymer, polyethylmethacrylate-2-hydroxyethylmethacrylate copolymer, polypropylmethacrylate-2-hydroxyethylmethacrylate copolymer, polybutylmethacrylate-2-hydroxyethylmethacrylate copolymer, polymethylacrylate-2-hydroxyethylmethacrylate copolymer, polyethylacrylate-2-hydroxyethylmethacrylate copolymer, polypropylacrylate-2-hydroxymethacrylate copolymer, polybutylacrylate-2-hydroxyethylmethacrylate copolymer, copolymermethylvinylether maleicanhydride copolymer, poly (2-hydroxyethyl methacrylate) and a polyethylene oxide.

10. The stent of claim 1, wherein the active agent is selected from the group consisting of plasmin, streptokinase, single chain urokinase, urokinase, t-PA (tissue type plasminogen activator), aminocaproic acid, aspirin, monoclonal antibodies, peptides, ReoPro, Cilastagel, eptifibatide, tirofiban, ticlopidine, Vapiprost, dipyridamole, forskolin, angiopeptin, argatroban, dextan, heparin, LMW heparin, a heparin complex, Enoxaparin, Dalteparin, hirudin, recombinant hirudin, antithrombin, a synthetic antithrombin, a thrombin inhibitor, Warfarin, a coumarin, vincristine, vinblastine, paclitaxel, a paclitaxel analogue, methotrexate, cisplatin, fluorouracil, rapamycin, azathioprine, cyclophosphamide, mycophenolic acid, a corticosteroid, colchicine, nitroprusside, angiostatin, endostatin, genetic material, an oligonucleotide, Cilazapril, Lisinopril, Captopril, VEGF, FGF, Probucol, Tocopherol, nifedipine, Molsidomine, angiopeptin, prednisolone, a glucocorticoid, dexamethasone, rifamycin, Re-188, Re-186, 1-125, Y-90, celecoxib, Vioxx, theophylline, tacrolimus, everolimus, sirolimus and combinations.

11. The stent of claim 1, wherein the active agent comprises heparin together with an antirestenotic drug selected from the group consisting of paclitaxel, rapamycin, sirolimus, everolimus, tacrolimus, and combinations.

12. The stent of claim 1, wherein the active agents are benzalkonium heparinate and paclitaxel.

13. The stent of claim 1, wherein the primer layer comprises an ethylene acrylic acid copolymer and an epoxy polymer, and wherein the ethylene acrylic acid copolymer is one or more of PRIMACOR™ 5989 and 5990 and the epoxy is one or more of EPOTUF™ 38-505, EPOTUF™ 37-618, and EPON™ 1001.

14. The stent of claim 1, wherein the drug reservoir layer comprises a polyurethane and a cellulose nitrate.

15. The stent of claim 14, wherein the polyurethane is polytetramethylene ether glycol urethane, polycarbonate urethane or combinations thereof.

16. The stent of claim 14, wherein the polyurethane is selected from the group consisting of CHRONOFLEX® AR, CHRONOFLEX® AL, CHRONOFLEX® C and BIONATE® 80A.

17. The stent of claim 1, wherein the primer layer comprises an ethylene acrylic acid copolymer and an epoxy polymer and the drug reservoir layer comprises a polyurethane and a cellulose ester.

* * * * *